(12) United States Patent
Park et al.

(10) Patent No.: US 7,851,654 B2
(45) Date of Patent: Dec. 14, 2010

(54) CHALCONE DERIVATIVES, PHARMACEUTICALLY ACCEPTABLE SALT, METHOD FOR PREPARATION AND USES THEREOF

(75) Inventors: Ki Hun Park, Jinju (KR); Jin Hyo Kim, Masan (KR); Woo Duck Seo, Jinju (KR); Young Bae Ryu, Namyun (KR); Hyung Won Ryu, Masan (KR); Woo Song Lee, Daejeon (KR); Sang Wan Gal, Jinju (KR)

(73) Assignee: Industry-Academic Cooperation Foundation Gyeongsang National University, Jinju (KR)

( * ) Notice: Subject to any disclaimer, the term of this patent is extended or adjusted under 35 U.S.C. 154(b) by 0 days.

(21) Appl. No.: 12/295,669

(22) PCT Filed: Apr. 3, 2006

(86) PCT No.: PCT/KR2006/001227

§ 371 (c)(1),
(2), (4) Date: Jan. 5, 2009

(87) PCT Pub. No.: WO2007/114532

PCT Pub. Date: Oct. 11, 2007

(65) Prior Publication Data

US 2009/0252694 A1    Oct. 8, 2009

(51) Int. Cl.
*C07C 211/00*   (2006.01)
*A61K 31/13*    (2006.01)
*A61K 31/135*   (2006.01)

(52) U.S. Cl. .................. 564/384; 514/655; 514/676; 514/685

(58) Field of Classification Search ............. 564/384; 514/655, 676, 685
See application file for complete search history.

(56) References Cited

U.S. PATENT DOCUMENTS 4,279,930 A    7/1981   Hall et al.

FOREIGN PATENT DOCUMENTS

WO   9101824    2/1991
WO   03037315   5/2003

OTHER PUBLICATIONS

Ansari et al. Combinatorial Synthesis and Antibacterial Evaluation of an Indexed Chalcone Library. Chemistry & Biodiversity, 2005, vol. 2, p. 1656-1664.*

Upadhyay et al. Studies on pyrzolines. HCAPLUS, Accession No. 1992:128768; Document No. 116:128768, 1991.*
Bertozzi, C. R. et al., Chemical Glycobiology, Science, 2001, pp. 2357-2364, vol. 291.
Moremen, K. W. et al., Glycosidases of the Asparagine-linked Oligosaccharide Processing Pathway, Glycobiology, 1994, pp. 113-125, vol. 4(2).
Robinson, K. M. et al., New Potent α-Glucohydrolase Inhibitor MDL 73945 with Long Duration of Action in Rats, Diabetes, 1991, pp. 825-830, vol. 40.
Dwek, R. A., et al., Targeting Glycosylation as a Therapeutic Approach, Nature Reviews Drug Discovery, 2002, pp. 65-75, vol. 1.
Fernandes, B. et al., β1-6 Branched Oligosaccharides as a Marker of Tumor Progression in Human Breast and Colon Neoplasia, Cancer Research, 1991, pp. 718-723, vol. 51.
Mehta, A. et al, α-Glucosidase Inhibitors as Potential Broad Based Anti-viral Agents, FEBS Letters, 1998, pp. 17-22, vol. 430.
Nerya, O. et al., Glabrene and Isoliquiritigenin as Tyrosinase Inhibitors from Licorice Roots, Journal of Agricultural and Food Chemistry, 2003, pp. 1201-1207, vol. 51(5).
Maeda, K. et al., In vitro Effectiveness of Several Whitening Cosmetic Components in Human Melanocytes, J. Soc. Cosmet. Chem., 1991, pp. 361-368, vol. 42.
Chen, J. S. et al., Inhibitory Effect of Kojic Acid on Some Plant and Crustacean Polyphenol Oxidases, Journal of Agricultural and Food Chemistry, 1991, pp. 1396-1401, vol. 39(8).
Mehta K.J. et al, Preparation and Antimicrobial Activity of Chalcones Derived from 4-(p-TOLYL/p-Chlorobenzenesulphonamido-Acetophenone, J. Inst. Chemists (India), 1979, pp. 60-61, vol. 51.
Seo, W. D. et al, Sulfonamide Chalcone as a New Class of α-Glucosidase Inhibitors, Bioorganic & Medicinal Chemistry Letters, 2005, pp. 5514-5516, vol. 15.
Fernandes, Y. J. et al, Studies on Pyrazoline. Part II. Preparation and Antimicrobial Activity of 3-(3'-Phenylsulphonamidophenyl)-5-aryl-1H/phenyl/acetyl pyrazolines, J. Indian Chem. Soc., 1997, p. 238, vol. 74.

* cited by examiner

*Primary Examiner*—Sikarl A Witherspoon
(74) *Attorney, Agent, or Firm*—Lucas & Mercanti, LLP

(57) ABSTRACT

Disclosed relates to a novel chalcone derivative, pharmaceutically acceptable salt thereof, a method for preparing the same and uses thereof, the chalcone derivative being readily obtained through the steps of: reacting aminoacetophenone with sulfonylchloride under the presence of an appropriate salt; and reacting the compound prepared in the above step with hydroxybenzaldehyde under the presence of an appropriate catalyst. The chalcone derivative of formula 1 in accordance with the present invention having strong enzyme inhibitory activities for glycosidase can be effectively used in preventing and treating various diseases induced by glycosidase, and the chalcone derivative of the invention having tyrosinase and melanin synthesis inhibitory activities can be effectively used as a skin-whitening compound.

15 Claims, No Drawings

CHALCONE DERIVATIVES, PHARMACEUTICALLY ACCEPTABLE SALT, METHOD FOR PREPARATION AND USES THEREOF

CROSS-REFERENCE TO RELATED APPLICATIONS

This application is a 371 of PCT/KR2006/001227 filed on Apr. 3, 2006, the contents of which are incorporated herein by reference.

TECHNICAL FIELD

The present invention relates to novel chalcone derivatives, pharmaceutically acceptable salts thereof, a method for preparing the same and uses thereof.

BACKGROUND ART

Chalcones, considered as the precursor of flavonoids and isoflavonoids, are abundant in edible plants. Chalcone derivatives as an ingredient of yellow pigments in plants influence the colors of the plants and protect the plants from ultraviolet rays as well. The chalcone derivatives are abundant in Coreopsis, one of the compositae plants. Representative chalcones include 2',6'-dihydroxy-4'-metoxychalcone, carthamin, etc., which are contained in the plants such as cinnamon, safflower, pepper, etc. Dihydrochalcones are contained primarily in rosaceae and ericaceae plants. One of the dihydrochalcones such as phloridzin, which is in the apples is related to the resistibility for diseases of the apples. It has been well known that such chalcone derivatives display a diverse array of pharmacological activities, such as anti-protozoal (Liu, M. et. al., J. Med. Chem. 2001, 44, 4443), anti-inflammatory (Babu, M. A., et. al., Bioorg. Med. Chem. 2003, 10, 4035), immuno-modulatory (Barfod, L., et. al., Int. Immunopharmacol. 2002, 2, 545), nitric oxide inhibitory (Rojas, J., et. al., Bioorg. Med. Chem. Lett. 2002, 12, 1951), anticancer (Kumar, S. K., et. al., J. Med. Chem. 2003, 46, 2813), anti-HIV activities (Artico, M., et. al., J. Med. Chem. 1998, 41, 3984), etc.

Meanwhile, glycosidases are enzymes that hydrolyze sugar chains in the process of metabolisms of carbohydrate and glycoprotein to be degraded into monosaccharides or the other absorbable polysaccharides. These glycosidases are responsible for the processing and synthesis of complex carbohydrates, which are essential in numerous biological recognition processes (Bertozzi, C. R. et. al, Science 2001, 291, 2357; Morenem, K. W. et. al., Glycobiology 1994, 4, 113).

Recently, various attempts to try to screen glycosidase inhibitors have been made actively. For example, it has been reported that glycosidase inhibitors may be used as antidiabetic agents or antiobestic agents, since a variety of glycosidases participate in the food digestive system by degrading polysaccharides, such as starch, sucrose and the like, and oligosaccharides (Diabetes 1991, 40, 825-830).

Moreover, glycosidase inhibitors competitively inhibit the formation of glycosidases that participate in the process of forming mature glycoproteins from lipid-linked oligosaccharide intermediate. Accordingly, while the glycoproteins pass through endoplasmic reticulum to Golgi bodies, glycosidase inhibitors control the metabolism of such enzymes for sugar moieties of glycoproteins, thus inhibiting the formation of normal glycoproteins in cells (Nat. Rev. Drug Discov. 2002, 1, 65-75). As a result, signal transductions in cells, between cells and between tissues are disturbed to accumulate immature glycoproteins, thus inhibiting virus to couple with receptors of host cells and suppressing the formation of syncytiums required for the osmosis of host cell and virus. Consequently, the breeding of virus is inhibited. It has been reported that glycosidase inhibitors may be effectively used as anti-cancer agents (Cancer Res. 1991, 51, 718-723) and anti-viral agents (FEBS Lett. 1998, 430, 17-22).

Glycosidase inhibitors developed in the prior art include aza sugars (Kato, A. et al., J. Med. Chem. 2005, 48, 2036), isoxazoles (Schaller, C. et al., Bioorg. Med. Chem. Lett. 1999, 9, 277) and aminosugars (Chen, X. et al., Chem. Rev. 2003, 103, 1955). However, most of such glycosidase inhibitors are sugar mimics, of which syntheses require tedious multi-steps from carbohydrate or non-carbohydrate.

Meanwhile, it has been known that some of the chalcone based compounds described above have tyrosinase inhibitory activities (N. Ohad. et. al., J. Agric. Food Chem. 2003, 51, 1201). Tyrosinase (EC. 1. 14. 18. 1) is known to be the most important enzyme in melanin biosynthesis occurring in the cells of plants, microorganisms and mammals. This enzyme converts tyrosine to dihydroxyphenylalanine (DOPA), which is then converted to dopaquinone. This dopaquinone in turn can be readily converted to dopachrome, which is consequently converted to the black or brown melanins (G. Prota, 1992, Melanins and Melanogenesis). Such melanins existing in skin play an important role of protecting the body from ultraviolet rays and the like. However, an overproduction of melanin causes liver spots, freckles, etc., which accelerates skin aging, and is known to be one of the factors causing skin cancer. Accordingly, melanin synthesis inhibitors have been utilized as materials of skin-whitening cosmetics and agents for treating localized hyper-pigmentation (K, Maeda, J. Soc. Comet. Chem., 1991, 42, 361).

In the prior art, p-methoxyphenol, hydroquinone, kojic acid or arbutin were used as melanin synthesis inhibitors. However, their melanin inhibitory activities are weak or such inhibitors may cause side effects in that they damage the intrinsic functions of cells by denaturalizing pigment cells.

Moreover, with the object of inhibiting the melanin synthesis, vitamin C and its derivatives have been used. However, their tyrosinase inhibitory activities are also very low. Accordingly, new inhibitors for inhibiting tyrosinase activities and melanin syntheses even with a small dose and having a low cytotoxicity must be developed without delay (Chen, J., J. Agric. Food., 1991, 39).

The inventors of the present invention paying attention to the fact that there have been no researches on the chalcone derivatives, although the chalcone derivatives described above have excellent pharmacological activities, have synthesized a variety of novel chalcone derivatives having glycosidase inhibitory activities. Furthermore, the inventors of the present invention discovering that the chalcone derivatives of the present invention have tyrosinase and melanin synthesis inhibitory activities have completed the present invention by demonstrating that such derivatives can be used as a skin-whitening composition.

DISCLOSURE

Technical Problem

Accordingly, an object of the present invention is to provide novel chalcone derivatives.

Another object of the present invention is to provide a method for preparing the chalcone derivatives.

A still another object of the present invention is to provide pharmaceutical compositions for preventing and treating diseases caused by glycosidases as a use of the chalcone derivatives or pharmaceutically acceptable salts thereof.

A Yet another object of the present invention is to provide skin-whitening compositions for inhibiting tyrosinase activities and melanin synthesis activities as the other use of the chalcone derivatives or pharmaceutically acceptable salts thereof.

Technical Solution

To accomplish the above technical object, the present invention provides novel chalcone derivatives.

Moreover, the present invention provides a method for preparing the chalcone derivatives.

In addition, the present invention provides pharmaceutical compositions for preventing and treating diseases caused by glycosidases as a use of the chalcone derivatives or pharmaceutically acceptable salts thereof.

Furthermore, the present invention provides skin-whitening compositions for inhibiting tyrosinase activities and melanin synthesis activities as the other use of the chalcone derivatives or pharmaceutically acceptable salts thereof.

ADVANTAGEOUS EFFECTS

According to the present invention, novel chalcone derivates can be obtained. Moreover, the chalcone derivative of formula 1 in accordance with the present invention can be effectively used for preventing and treating diseases caused by glycosidases including α-glucosidase, α-amylase, β-amylase, etc., since the chalcone derivative shows strong enzyme inhibitory activities for such glycosidases. Furthermore, according to the present invention, the chalcone derivative of formula 1 having excellent tyrosinase and melanin synthesis inhibitory activities can be effectively applied to skin-whitening medicines and cosmetics.

BEST MODE

Hereinafter, the present invention will now be described in detail.

The present invention provides a chalcone derivative represented by formula 1 below or pharmaceutically acceptable salts thereof.

[Formula 1]

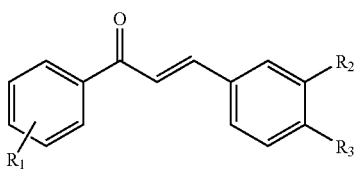

wherein $R_1$ is hydrogen, hydroxy group or $R_4NH$—;

$R_2$ and $R_3$ are hydrogen or hydroxy group, respectively and independently;

$R_4$ is hydrogen or $R_5SO_2$—; and $R_5$ is $C_1$~$C_5$ alkyl or $C_6$~$C_{10}$ aryl having at least one substituent selected from the group consisting of hydrogen, halogen, nitro and $C_1$~$C_6$ alkyl, preferably, methyl, benzyl, p-toluoyl, P-nitrophenyl or p-fluorophenyl among them.

Moreover, in the chalcone derivative represented by formula 1 in accordance with the present invention, it is desirable that the substituent $R_1$ is substituted on one of the 3- and 4-position in the benzene ring.

Desirable examples of the chalcone derivative represented by formula 1 in accordance with the present invention are as follows.
1) 4'-(p-toluenesulfonylamino)-3,4-dihydroxychalcone;
2) 4'-(p-toluenesulfonylamino)-4-hydroxychalcone;
3) 4'-benzenesulfonylamino-4-hydroxychalcone;
4) 4-(p-nitrobenzenesulfonylamino)-4-hydroxychalcone;
5) 4'-(p-fluorobenzenesulfonylamino)-4-hydroxychalcone;
6) 4'-methanesulfonylamino-4-hydroxychalcone;
7) 4'-amino-3,4-dihydroxychalcone;
8) 4'-amino-4-hydroxychalcone;
9) 4'-benzenesulfonylamino-3,4-dihydroxychalcone;
10) 4'-(p-nitrobenzenesulfonylamino)-3,4-dihydroxychalcone;
11) 4'-(p-fluorobenzenesulfonylamino)-3,4-dihydroxychalcone;
12) 4'-methanesulfonylamino-3,4-dihydroxychalcone;
13) 3'-amino-4-hydroxychalcone;
14) 3'-(p-toluenesulfonylamino)-4-hydroxychalcone;
15) 3'-amino-3,4-dihydroxychalcone;
16) 3'-(p-toluenesulfonylamino)-3,4-hydroxychalcone;
17) 4-hydroxychalcone; and
18) 4',4-dihydroxychalcone.

The chalcone derivatives represented by formula 1 in accordance with the present invention can be used in the form of pharmaceutically acceptable salts. Acid added salts formed by pharmaceutically acceptable free acids are most useful as such salts. The chalcone derivatives represented by formula 1 can be formed as pharmaceutically acceptable acid added salts in ordinary methods well known in the art. As free acids, inorganic acids and organic acids may be utilized, the inorganic acids including hydrochloric acid, bromic acid, sulfuric acid, phosphoric acid, etc., and the organic acids including citric acid, acetic acid, lactic acid, maleic acid, fumarinic acid, gluconic acid, methanesulfonic acid, glyconic acid, succinic acid, tartaric acid, 4-toluenesulfonic acid, galacturonic acid, embonic acid or aspartic acid. Preferably, the hydrochloric acids may be used as inorganic acid and the methanesulfonic acids may be applied as organic acid. Moreover, the chalcone derivatives represented by formula 1 in accordance with the present invention may include pharmaceutically acceptable salts and all salts, hydrates and solvates as well, which can be prepared in ordinary methods well known in the art.

The present invention provides a method for preparing chalcone derivatives represented by formula 1.

Particularly, the preparing method in accordance with the present invention, as represented by scheme 1 below, comprises the steps of: preparing a compound of formula 3 by reacting a compound of formula 2 with sulfonylchloride ($R_4SO_2Cl$) under the presence of an appropriate base [ST 1]; and preparing a compound of formula 1 by reacting the compound of formula 3 prepared in step 1 with hydroxybenzaldehide under the presence of an appropriate catalyst [ST 2].

[Scheme 1]

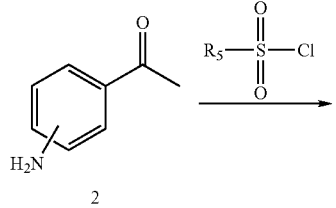

2

-continued

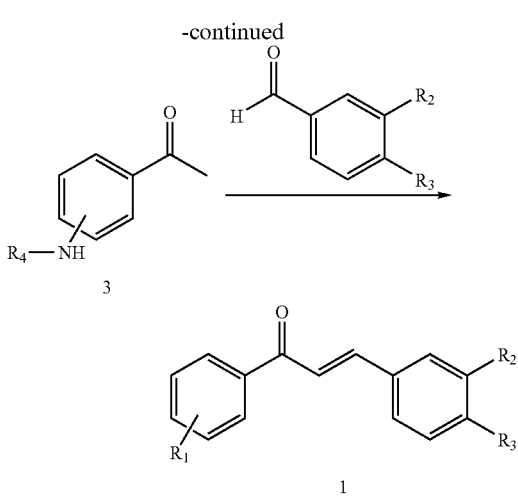

wherein $R_1$, $R_2$, $R_3$, $R_4$ and $R_5$ are the same as defined in formula 1.

The preparing method of the present invention will now be described step by step.

In the preparing method in accordance with the present invention, the base used in step 1 is desirably aromatic amines, such as pyridine, lutidine, etc., and tertiary amines, such as triethylamine, tripropylamine, N-methylmorpholine, etc., and preferably pyridine.

In the preparing method in accordance with the present invention, the solvent used in step 1 is desirably chloroform, dichloromethane, etc., preferably dichloromethane.

In the preparing method in accordance with the present invention, it is desirable to carry out the reaction in step 1 at room temperature for 1 to 24 hours.

The compounds 3 prepared as a result of carrying out step 1 may be formed as crystalline compounds, and such compounds may be separated using ordinary techniques such as recrystallization method using polarity difference in solvents.

In the preparing method in accordance with the present invention, it is desirable to use sulfuric acid as catalyst in step 2 and use alcohol such as methanol or ethanol as solvent.

The chalcone derivative of formula 1 prepared as a result of carrying out step 2 may be formed as a mixture with by-products. In such case, it is natural to separate the mixture in ordinary manners such as column chromatography.

Furthermore, the present invention provides a use of the chalcone derivative represented by formula 1 or pharmaceutically acceptable salts thereof.

Specifically, the chalcone derivatives represented by formula 1 or pharmaceutically acceptable salts thereof can be used as a composition comprising the same as an effective ingredient for inhibiting glycosidase activities. In this case, the glycosidases, of which activities are inhibited by such composition, include α-glucosidase, α-amylase, β-amylase, etc.

Glycosidase inhibitors that inhibit the glycosidase activities may be used as antidiabetic agents or antiobestic agent, since a variety of glycosidases participate in the food digestive system by degrading polysaccharides, such as starch, sucrose and the like, and oligosaccharides (Diabetes 1991, 40, 825-830). Accordingly, the composition comprising the chalcone derivatives as an effective ingredient in accordance with the present invention and having glycosidase inhibitory activities can be effectively used as agents for preventing and treating diabetes, obesity, etc.

Moreover, the composition comprising the chalcone derivative as an effective ingredient in accordance with the present invention and having glycosidase inhibitory activities competitively retards glycosidases that participate in the process of forming mature glycoproteins from lipid-linked oligosaccharide intermediate, thus inhibiting the formation of normal glycoproteins in cells. As a result, signal transductions in cells, between cells and between tissues are disturbed to accumulate immature glycoproteins, thus inhibiting virus to couple with receptors of host cells and suppressing the formation of syncytiums required for the osmosis of host cell and virus. Consequently, the breeding of virus is inhibited. The composition comprising the chalcone derivative as an effective ingredient in accordance with the present invention can be effectively used for preventing and treating cancers or viral diseases, e.g., human immunodeficiency virus (HIV) or hepatitis B virus (HBV).

In addition, the present invention provides the other use of the chalcone derivatives represented by formula 1 or pharmaceutically acceptable salts thereof.

That is, the composition comprising the chalcone derivatives of formula 1 or pharmaceutically acceptable salts thereof may inhibit tyrosinase activities that synthesize melanin from tyrosine, thus preventing the melanin synthesis.

Particularly, it has been proved experimentally that the chalcone derivative of formula 1 in accordance with the present invention have excellent inhibitory effects in comparison with the conventional p-methoxyphenol, kojic acid or arbutin being used as inhibitors for inhibiting tyrosine activities and melanin synthesis activities.

Furthermore, the composition comprising the chalcone derivative of formula 1 or pharmaceutically acceptable salts thereof may inhibit black or brown melanin synthesis, thus being effectively used as skin-whitening medicines and cosmetics.

In cases where the compositions of the present invention are used as medicines, the compound comprising the chalcone derivative represented by formula 1 or pharmaceutically acceptable salts thereof may be administered in various forms formulated for oral or parenteral administrations as described below, which, however, are not limited thereto.

For formulations, commonly used diluents or excipients such as fillers, expanders, bonding agents, humectants, disintegrants, surfactants, etc. are used. Solid dosages for oral administration include tablets, pillets, powders, granules, capsules, etc. Such solid dosages are prepared by admixing the compound of the present invention with at least one excipient, such as starch, calcium carbonate, sucrose or lactose, gelatin, etc. In addition to simple expedients, lubricants such as magnesium styrate, talc, etc. may be added. Liquid dosage forms for oral administration, such as suspensions, internal solutions, emulsions, syrups, etc., may comprise simple diluents, e.g., water and liquid paraffin, as well as various excipients, e.g., humectants, sweeteners, aromatics, preservatives, etc. Dosage forms for parenteral administration include sterilized aqueous solutions, non-aqueous solvents, suspensions, emulsions, lyophilized agents, suppositories, etc. Non-aqueous solvents and suspensions may be prepared using vegetable oils, such as propylene glycol and polyethylene glycol, olive oil, or using injectable esters such as ethyloleate.

The dosages of the compound in accordance with the present invention may be varied according to various relevant factors, such as weight, age, sex and health status of patients, time and method of administration, and severity of symptoms. Concretely, on the basis of an adult patient of 70 kg, a total dosage is generally 0.1 to 1,000 mg a day and, preferably, 1 to 500 mg a day. Moreover, it is possible to administrate such compound to the patient once to several times a day at regular intervals in compliance with a doctor's decision.

In addition, when the compound of the present invention is applied to cosmetics, the compound represented by formula 1 or pharmaceutically acceptable salt thereof may be applied to basic skincare cosmetic products, such as face lotion, cream, essence, cleansing form, cleansing water, pack, etc.; body cosmetic products, such as body lotion, body oil, body gel, etc.; color cosmetic products, such as foundation, lipstick, mascara, makeup base, etc.; and hair cosmetic products, such as shampoo, rinse, hair conditioner, hair gel, etc., by mixing the compound of the present invention in the ratio of 0.01 to 20.0 weight % for dry weights of such cosmetic materials.

Moreover, when applying the compound of formula 1 of the present invention to foods, the compound may be mixed in the content of 0.01 to 20.0 weight % for dry weights of various foods.

MODE FOR INVENTION

Hereinafter, the present invention will now be described more fully with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Example 1

Preparation of 4'-(p-toluenesulfonylamino)-3,4-dihydroxychalcone

Step 1 Preparation of 4-p-toluenesulfonylaminoacetophenone 1.53 g of 4-aminoacetophenone (11.3 mmol) and 2.59 g of p-toluenesulfonylchloride (13.6 mmol) were diluted with 100 ml of dichloromethane and, then, the resultant solution was put into 1.10 ml of pyridine solvent (13.6 mmol) to be stirred at room temperature for three hours. The resultant solution was washed with a saturated sodium bicarbonate solution until the pH became 8. Aqueous layer was extracted with 100 ml of dichloromethane three times. Organic layer was all collected to be dried with sodium sulfate and, then, concentrated under reduced pressure. The resultant mixture was recrystallized in a solvent mixed with dichloromethane, diethylether and hexane, thus obtaining a target compound of 3.14 g (96%).

$^1$H NMR (300 MHz, CDCl3) d 2.41 (3H, s), 2.55 (3H, s), 7.09 (1H, s), 7.16 (2H, d, J=8.3 Hz), 7.28 (2H, m), 7.75 (2H, d, J=8.6 Hz), 7.87 (2H, d, J=8.6 Hz)

Step 2: Preparation of 4'-(p-toluenesulfonylamino)-3,4-dihydroxychalcone 2.50 g of 4-p-toluenesulfonylaminoacetophenone (8.6 mmol) obtained in step 1 and 1.43 g of 3,4-dihydroxybenzaldehyde (10.4 mmol) were melted in 100 ml of methanol and the resultant solution was subjected to reflux under the presence of 0.5 ml of sulfuric acid at room temperature for eight hours. After concentrating the solvent under reduced pressure, 150 ml of ethylacetate was added thereto to melt and, then, washed with saturated sodium bicarbonate solution until the pH became 8. Aqueous layer was extracted with 100 ml of ethylacetate three times. Organic layer was all collected to be dried with sodium sulfate and, then, concentrated under reduced pressure. The resultant mixture was separated with silica gel column chromatography, thus obtaining a target compound (yellow powders, 2.94 g, 83%).

Melting point: 180 to 181° C.

$^1$H NMR (300 MHz; MeOD+DMSO-$d_6$) d 2.29 (3H, s), 6.78 (1H, d, J=8.2 Hz), 6.94 (1H, dd, $J_1$=8.2, $J_2$=2.0 Hz), 7.10 (1H, d, J=2.0 Hz), 7.19 (5H, m), 7.50 (1H, d, J=15.2 Hz), 7.66 (2H, d, J=8.2 Hz), 7.76 (2H, d, J=8.6 Hz)

HERIMS m/z 409.0984 [M$^+$] (calcd for $C_{22}H_{19}NO_5S$, 409.0983)

Example 2

Preparation of 4'-(p-toluenesulfonylamino)-4-hydroxychalcone

A target compound (2.77 g of yellow powders, 82%) was obtained in the same manner as Example 1 except for using 4-hydroxybenzaldehyde instead of 3,4-dihydroxybenzaldehide in step 2 of Example 1.

Melting point: 106 to 107° C.

$^1$H NMR (300 MHz; MeOD) d 2.25 (3H, s), 6.82 (2H, d, J=8.6 Hz), 7.23 (4H, m), 7.42 (1H, d, J=15.5 Hz), 7.51 (2H, d, J=8.6 Hz), 7.66 (1H, d, J=15.5 Hz), 7.73 (2H, d, J=8.3 Hz), 7.90 (2H, dd, $J_1$=8.7, $J_2$=2.0 Hz)

HERIMS m/z 393.1035 [M$^+$] (calcd for $C_{22}H_{19}NO_4S$, 393.1034)

Example 3

Preparation of 4'-benzenesulfonylamino-4-hydroxychalcone

A target compound (2.85 g of yellow powders, 80%) was obtained in the same manner as Example 1 except for using benzenesulfonylchloride instead of p-toluenesulfonylchloride in step 1 of Example 1 and using 4-hydroxybenzaldehyde instead of 3,4-dihydroxybenzaldehyde in step 2 of Example 1.

Melting point: 98 to 99° C.

$^1$H NMR (300 MHz; MeOD) d 6.84 (1H, d, J=8.6 Hz), 7.27 (2H, d, J=8.7 Hz), 7.55 (6H, m), 7.71 (1H, d, J=15.5 Hz), 7.88 (2H, d, J=8.6 Hz), 7.96 (2H, d, J=8.7 Hz)

HERIMS m/z 379.0878 [M$^+$] (calcd for $C_{21}H_{17}NO_4S$, 379.0875)

Example 4

Preparation of 4'-(p-nitrobenzenesulfonylamino)-4-hydroxychalcone

A target compound (2.81 g of yellow powders, 85%) was obtained in the same manner as Example 1 except for using p-nitrobenzenesulfonylchloride instead of p-toluenesulfonylchloride in step 1 of Example 1 and using 4-hydroxybenzaldehyde instead of 3,4-dihydroxybenzaldehyde in step 2 of Example 1.

Melting point: 90 to 91° C.

$^1$H NMR (300 MHz; MeOD) d 6.72 (2H, d, J=8.6 Hz), 7.14 (4H, m), 7.32 (1H, d, J=15.5 Hz), 7.41 (2H, d, J=8.6 Hz), 7.54 (1H, d, J=15.5 Hz), 7.62 (2H, d, J=8.3 Hz), 7.80 (2H, dd, $J_1$=8.7, $J_2$=2.0 Hz)

HERIMS m/z 424.0729 [M$^+$] (calcd for $C_{21}H_{16}N_2O_6S$, 424.0727)

Example 5

Preparation of 4'-(p-fluorobenzenesulfonylamino)-4-hydroxychalcone

A target compound (2.77 g of brown powders, 82%) was obtained in the same manner as Example 1 except for using p-fluorobenzenesulfonylchloride instead of p-toluenesulfonylchloride in step 1 of Example 1 and using 4-hydroxybenzaldehide instead of 3,4-dihydroxybenzaldehide in step 2 of Example 1.

Melting point: 101 to 102° C.

$^1$H NMR (300 MHz; MeOD) d 6.87 (2H, d, J=8.6 Hz), 7.28 (4H, m), 7.59 (1H, d, J=15.4 Hz), 7.68 (2H, d, J=8.6 Hz), 7.89 (1H, d, J=15.5 Hz), 7.91 (2H, d, J=8.5 Hz), 7.96 (2H, dd, $J_1$=8.6)

HERIMS m/z 397.0784 [M$^+$] (calcd for $C_{21}H_{16}FNO_4S$, 397.0783)

Example 6

Preparation of 4'-(methanesulfonylamino)-4-hydroxychalcone

A target compound (3.04 g of yellow powders, 82%) was obtained in the same manner as Example 1 except for using methanesulfonylchloride instead of p-toluenesulfonylchloride in step 1 of Example 1 and using 4-hydroxybenzaldehyde instead of 3,4-dihydroxybenzaldehyde in step 2 of Example 1.

Melting point: 85 to 86° C.

$^1$H NMR (300 MHz; MeOD) d 3.08 (3H, s), 6.86 (2H, d, J=8.6 Hz), 7.37 (2H, d, J=8.7 Hz), 7.58 (1H, d, J=15.5 Hz), 7.62 (2H, d, J=8.6 Hz), 7.75 (1H, d, J=15.4 Hz), 8.07 (2H, d, J=8.8 Hz)

HERIMS m/z 317.0722 [M$^+$] (calcd for $C_{16}H_{15}NO_4S$, 317.0720)

Example 7

Preparation of 4'-amino-3,4-dihydroxychalcone

A target compound (3.91 g of pink powders, 83%) was obtained in the same manner as step 2 of Example 1 except for using 4-aminoacetophenone instead of 4-p-toluenesulfonylacetophenone.

Melting point: 184 to 185° C.

$^1$H NMR (300 MHz; MeOD) d 6.57 (2H, dd, $J_1$=8.8, $J_2$=1.9 Hz), 6.83 (2H, d, J=9.0 Hz), 7.08 (1H, dd, $J_1$=8.2, $J_2$=2.0 Hz), 7.18 (1H, d, J=2.0 Hz), 7.50 (1H, d, J=15.4 Hz), 7.62 (1H, d, J=15.5 Hz), 7.90 (2H, m) HERIMS m/z 255.0895 [M$^+$] (calcd for $C_{15}H_{13}NO_3$ 255.0894)

Example 8

Preparation of 4'-amino-4-hydroxychalcone

A target compound (3.53 g of pink powders, 80%) was obtained in the same manner as step 2 of Example 1 except for using 4-aminoacetophenone instead of 4-p-toluenesulfonylacetophenone and using 4-hydroxybenzaldehyde instead of 3,4-dihydroxybenzaldehyde.

Melting point: 80 to 81° C.

$^1$H NMR (300 MHz; MeOD) d 6.44 (2H, dd, $J_1$=6.9, $J_2$=1.9 Hz), 6.85 (2H, dd, $J_1$=6.9, $J_2$=1.8 Hz), 7.55 (3H, m), 7.68 (1H, d, J=15.5 Hz), 7.91 (2H, dd, $J_1$=7.9, $J_2$=2.0 Hz)

HERIMS m/z 239.0946 [M$^+$] (calcd for $C_{15}H_{13}NO_2$, 239.0944)

Example 9

Preparation of 4-benzenesulfonylamino-3,4-dihydroxychalcone

A target compound (2.94 g of yellow powders, 82%) was obtained in the same manner as Example 1 except for using benzenesulfonylchloride instead of p-toluenesulfonylchloride in step 1 of Example 1.

Melting point: 145 to 146° C.

$^1$H NMR (300 MHz; MeOD) d 3.36 (3H, s), 6.82 (1H, d, J=8.2 Hz), 7.02 (1H, d, J=8.7 Hz), 7.09 (1H, d, J=1.9 Hz), 7.27 (2H, d, J=8.6 Hz), 7.46 (1H, d, J=15.5 Hz), 7.56 (2H, m), 7.64 (1H, d, J=15.5 Hz), 7.87 (1H, d, J=8.7 Hz), 7.95 (1H, d, J=8.6 Hz)

HERIMS m/z 395.0827 [M$^+$] (calcd for $C_{21}H_{17}NO_5S$, 395.0825)

Example 10

Preparation of 4'-(p-nitrobenzenesulfonylamino)-3,4-hydroxychalcone

A target compound (2.74 g of yellow powders, 80%) was obtained in the same manner as Example 1 except for using p-nitrobenzenesulfonylchloride instead of p-toluenesulfonylchloride in step 1 of Example 1.

Melting point: 170 to 171° C.

$^1$H NMR (300 MHz; MeOD) d 6.68 (1H, d, J=8.2 Hz), 6.74 (1H, d, $J_1$=8.2, $J_2$=2.3 Hz), 6.98 (1H, d, J=2.0 Hz), 7.14 (5H, m), 7.50 (1H, d, J=15.5 Hz), 7.66 (2H, d, J=8.2 Hz), 7.84 (2H, d, J=8.7 Hz)

HERIMS m/z 440.0678 [M$^+$] (calcd for $C_{21}H_{16}N_2O_7S$, 440.0677)

Example 11

Preparation of 4'-(p-fluorobenzenesulfonylamino)-3,4-dihydroxychalcone

A target compound (3.52 g of brown powders, 82%) was obtained in the same manner as Example 1 except for using p-fluorobenzenesulfonylchloride instead of p-toluenesulfonylchloride in step 1 of Example 1.

Melting point: 183 to 184° C.

$^1$H NMR (300 MHz; MeOD) d 6.54 (1H, d, J=8.5 Hz), 6.61 (1H, dd, $J_1$=8.2), 7.12 (1H, d, J=2.0 Hz), 7.24 (2H, m), 7.34 (3H, m) 7.46 (1H, d, J=15.4 Hz), 7.58 (2H, d, J=8.6 Hz), 7.74 (2H, d, J=8.5 Hz)

HERIMS m/z 413.0733 [M$^+$] (calcd for $C_{21}H_{16}FNO_5S$, 413.0731)

Example 12

Preparation of 4'-(methanesulfonylamino)-3,4-dihydroxychalcone

A target compound (3.24 g of yellow powders, 83%) was obtained in the same manner as Example 1 except for using methanesulfonylchloride instead of p-toluenesulfonylchloride in step 1 of Example 1.

Melting point: 111 to 112° C.

$^1$H NMR (300 MHz; MeOD) d 3.09 (3H, s), 6.84 (1H, d, J=8.7 Hz), 7.13 (1H, d, J=8.6 Hz), 7.20 (1H, d, J=1.9 Hz), 7.38 (2H, d, J=8.6 Hz), 7.52 (1H, d, J=15.5 Hz), 7.69 (1H, d, J=15.5 Hz), 8.07 (2H, d, J=8.7 Hz)

HERIMS m/z 333.0671 [M$^+$] (calcd for $C_{16}H_{15}NO_5S$, 333.0670)

Example 13

Preparation of 3'-amino-4-hydroxychalcone

A target compound (3.63 g of white powders, 82%) was obtained in the same manner as step 2 of Example 1 except for using 3-aminoacetophenone instead of 4-p-toluenesulfonylaminoacetophenone and using 4-hydroxybenzaldehyde instead of 3,4-dihydroxybenzaldehyde.

Melting point: 80 to 81° C.

$^1$H NMR (300 MHz; MeOD) d 6.56 (1H, m), 6.68 (1H, d, J=8.5 Hz), 6.77 (3H, m), 7.13 (3H, m), 7.27 (1H, m), 7.75 (2H, dd, J$_1$=8.0, J$_2$=1.5 Hz)

HERIMS m/z 239.0946 [M$^+$] (calcd for $C_{15}H_{13}NO_2$, 239.0945)

Example 14

Preparation of 3'-(p-toluenesulfonylamino)-4-hydroxychalcone

A target compound (2.79 g of yellow powders, 82%) was obtained in the same manner as Example 1 except for using 3-aminoacetophenone instead of 4-aminoacetophenone in step 1 of Example 1 and using 4-hydroxybenzaldehyde instead of 3,4-dihydroxybenzaldehyde in step 2 of Example 1.

Melting point: 184 to 185° C.

$^1$H NMR (300 MHz; MeOD) d 2.35 (3H, s), 6.86 (2H, dd, J$_1$=6.8, J$_2$=1.9 Hz), 7.29 (2H, d, J=8.3 Hz), 7.37 (3H, m), 7.58 (2H, m), 7.69 (5H, m)

HERIMS m/z 393.1035 [M$^+$] (calcd for $C_{22}H_{19}NO_4S$, 393.1033)

Example 15

Preparation of 3'-amino-3,4-dihydroxychalcone

A target compound (3.92 g of yellow powders, 83%) was obtained in the same manner as step 2 of Example 1 except for using 3-aminoacetophenone instead of 4-p-toluenesulfonylaminoacetophenone.

Melting point: 185 to 186° C.

$^1$H NMR (500 MHz; MeOD) d 6.98 (1H, d, J=8.2 Hz), 7.2 (1H, s), 7.51 (3H, m), 7.62 (1H, s), 7.75 (1H, m), 8.01 (1H, d, J=8.4 Hz), 8.19 (1H, dd, J$_1$=8.3, J$_2$=1.9 Hz)

HERIMS m/z 255.0895 [M$^+$] (calcd for $C_{15}H_{13}NO_3$, 255.0893)

Example 16

Preparation of 3'-(p-toluenesulfonylamino-3,4-dihydroxychalcone

A target compound (2.83 g of yellow powders, 80%) was obtained in the same manner as Example 1 except for using 3-aminoacetophenone instead of 4-aminoacetophenone in step 1 of Example 1.

Melting point: 190 to 191° C.

$^1$H NMR (300 MHz; MeOD) d 2.35 (3H, s), 6.85 (1H, d, J=8.2 Hz), 7.07 (1H, dd, J$_1$=8.3, J$_2$=2.0 Hz), 7.18 (1H, d, J=2.0 Hz), 7.27 (2H, m), 7.39 (5H, m), 7.62 (1H, d, J=15.6 Hz), 7.68 (4H, m)

HERIMS m/z 409.0984 [M$^+$] (calcd for $C_{22}H_{19}NO_5S$, 409.0982)

Example 17

Preparation of 4-dihydroxychalcone

A target compound (3.96 g of yellow powders, 85%) was obtained in the same manner as step 2 of Example 1 except for using acetophenone instead of 4-p-toluenesulfonylacetophenon and using 4-hydroxybenzaldehyde instead of 3,4-dihydroxybenxaldehide.

Melting point: 187 to 188° C.

$^1$H NMR (300 MHz; MeOD) d 6.86 (2H, dd, J$_1$=6.70 Hz, J$_2$=1.8 Hz), 7.49-7.64 (6H, m), 7.75 (1H, d, J=15.5 Hz), 8.04 (2H, m)

HERIMS m/z 224.0837 [M$^+$] (calcd for $C_{15}H_{12}O_2$, 224.0837)

Example 18

Preparation of 4'4-dihydroxychalcone

A target compound (3.57 g of yellow powders, 81%) was obtained in the same manner as step 2 of Example 1 except for using 4-hydroxyacetophenone instead of 4-p-toluenesulfonylacetophenon and using 4-hydroxybenzaldehyde instead of 3,4-dihydroxybenxaldehide.

Melting point: 238 to 239° C.

$^1$H NMR (300 MHz; MeOD) d 6.85 (2H, dd, J$_1$=8.64 Hz, J$_2$=2.0 Hz), 6.90 (2H, dd, J$_1$=6.83, J$_2$=2.0 Hz), 7.52 (1H, d, J=15.6 Hz), 7.53 (2H, d, J=8.9 Hz), 7.70 (1H, d, J=15.5 Hz), 7.98 (2H, d, J$_1$=6.8 Hz, J$_2$=2.0 Hz)

HERIMS m/z 240.0786 [M$^+$] (calcd for $C_{15}H_{12}O_3$, 240.0786)

Structural formulas of chalcone derivatives in Examples 1 to 16 were shown in table 1 below.

TABLE 1

| EXAMPLES | STRUCTURES |
| --- | --- |
| 1 | 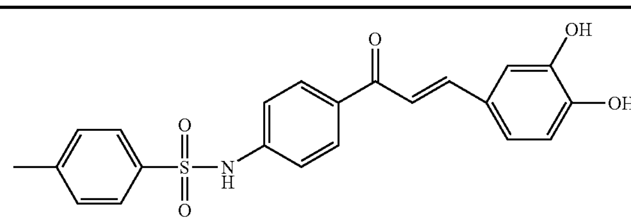 |

TABLE 1-continued
| EXAMPLES | STRUCTURES |
|---|---|
| 2 | 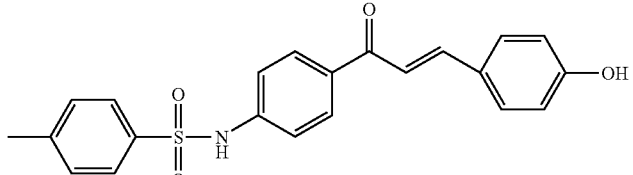 |
| 3 | 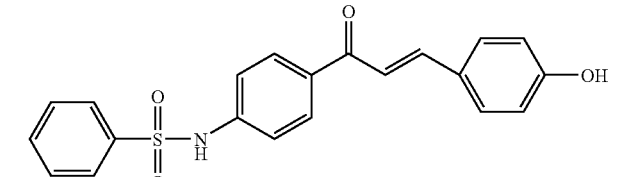 |
| 4 | 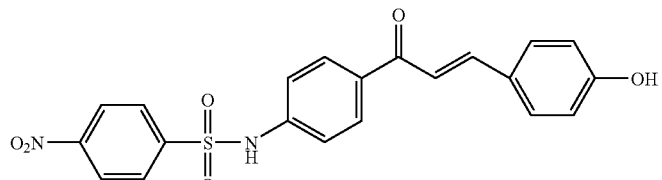 |
| 5 | 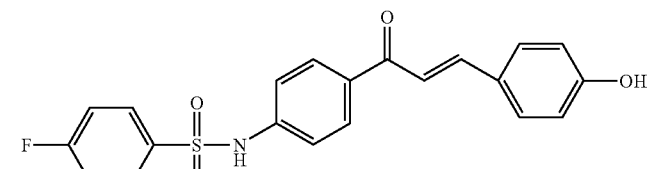 |
| 6 | 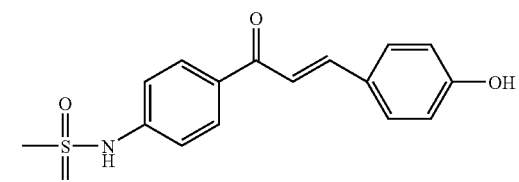 |
| 7 | 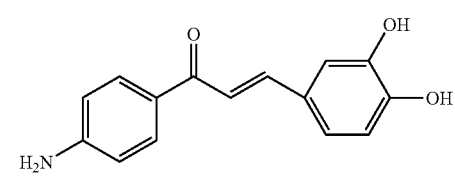 |
| 8 | 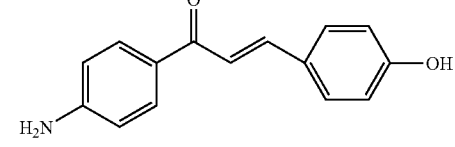 |
| 9 | 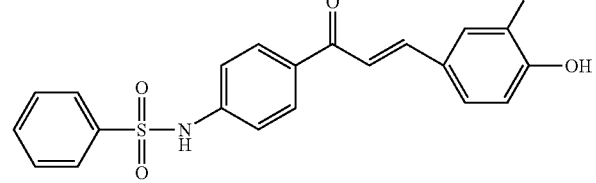 |

TABLE 1-continued

| EXAMPLES | STRUCTURES |
| --- | --- |
| 10 | 4-nitrophenylsulfonamide-N-(4-(3-(3,4-dihydroxyphenyl)acryloyl)phenyl) |
| 11 | 4-fluorophenylsulfonamide-N-(4-(3-(3,4-dihydroxyphenyl)acryloyl)phenyl) |
| 12 | methylsulfonamide-N-(4-(3-(3,4-dihydroxyphenyl)acryloyl)phenyl) |
| 13 | 1-(3-aminophenyl)-3-(4-hydroxyphenyl)prop-2-en-1-one |
| 14 | 4-methylphenylsulfonamide-N-(3-(3-(4-hydroxyphenyl)acryloyl)phenyl) |
| 15 | 1-(3-aminophenyl)-3-(3,4-dihydroxyphenyl)prop-2-en-1-one |
| 16 | 4-methylphenylsulfonamide-N-(3-(3-(3,4-dihydroxyphenyl)acryloyl)phenyl) |
| 17 | 1-phenyl-3-(4-hydroxyphenyl)prop-2-en-1-one |

TABLE 1-continued

| EXAMPLES | STRUCTURES |
|---|---|
| 18 | HO-C6H4-CO-CH=CH-C6H4-OH |

The following experiments were carried out in order to measure glycosidase inhibitory activities of the chalcone derivatives of formula 1 in accordance with the present invention.

Experimental Example 1

Measurement α-Glucosidase Inhibitory Activities of the Chalcone Derivatives of the Invention Via Nitrophenol Quantitative Analysis α-glucosidase, a kind of glycosidase enzymes, was used to identify glycosidase inhibitory activities of the chalcone derivatives of the present invention. Glycosidase activities were assessed using an amount of p-nitrophenyl produced when p-nitrophenyl-α-D-glucopyranoside as substrate was hydrolyzed by α-glucosidase (J. Med. Chem. 2005, 48, 2036-2044).

Glucosidases, extracted from baker's yeast, of 1 unit/ml were dissolved in potassium phosphate buffer (0.07 M, pH 6.8) on a 97 well plate and quantified as 100 μl. Subsequently, p-nitrophenyl-α-D-glucosidases as substrate were dissolved in the potassium phosphate buffer in a concentration of 5 mM and quantified as 100 μl. Next, the chalcone derivatives prepared in Examples 2, 5, 6, 8, 10 and 12 were dissolved in 50% DMSO solvent and quantified as 50 μl. The samples quantified were reacted at 37° C. for twenty minutes to measure absorbance at 405 nm, thus obtaining glucosidase inhibitory rates via equation 1 below. Measured $IC_{50}$ values of the chalcone derivatives prepared in Examples 2, 5, 6, 8, 10 and 12 for α-glucosidases were shown in table 2.

Inhibitory rate (%)=$(A-B)/A \times 100$ [Equation 1]

wherein A denotes an absorbance value measured of one to which inhibitors were added; and B denotes an absorbance value of one to which inhibitors were not added.

TABLE 2

| Chalcone derivatives | $IC_{50}$ (μM) |
|---|---|
| Example 2 | 0.98 |
| Example 5 | 62.10 |
| Example 6 | 0.40 |
| Example 8 | 41.00 |
| Example 10 | 12.40 |
| Example 12 | 15.60 |

As shown in table 2, it can be learned that the chalcone derivatives of Examples 2, 5, 6, 8, 10 and 12 in accordance with the present invention have very excellent α-glucosidase inhibitory activities as the $IC_{50}$ values measured are shown as 0.98, 62.1, 0.40, 41.0, 12.4 and 15.6, respectively.

Experimental Example 2

Measurement of α-Amylase Inhibitory Activities of the Chalcone Derivatives of the Invention Via Analysis of Reducing Sugars α-amylase, a kind of glycosidase enzymes, was used to identify glycosidase inhibitory activities of the chalcone derivatives of the present invention. Using 1% starch as substrate, α-amylase activities were measured by measuring the amounts in that α-amylases hydrolyzed the substrates after adding DNS (1% dinitrosalicylic acid, 12% potassium sodium tartrate in 0.4 M NaOH), a color reagent (Bioorg. Med. Chem. Lett., 2002, 12, 2335-2339). 1% starch as substrate was dissolved in acetate buffer (0.05 M, pH 4.5) in test tubes. After preprocessing at 37° C. for ten minutes, the resultant solutions were quantified as 100 μl in tubes. α-amylases of 0.25 unit/ml, prepared with the acetate buffer, were quantified as 100 μl. Subsequently, the chalcone derivatives prepared in Examples 2, 5, 6, 8, 9, 10, 11 and 12 in accordance with the present invention were dissolved in 50% DMSO solvent and quantified as 50 μl, respectively. After reacting the samples quantified at 37° C. for twenty minutes, 300 μl of DNS, the color reagent, were added thereto. Next, the resultant solutions were reacted in boiled water for ten minutes and cooled to measure absorbance at 540 nm, thus obtaining amylase inhibitory rates via equation 1 above. Measured $IC_{50}$ values of the chalcone derivatives prepared in Examples 2, 5, 6, 8, 9, 10, 11 and 12 for α-amylases were depicted in table 3.

TABLE 3

| | $IC_{50}$ (μM) | |
|---|---|---|
| Compound | α-amylase | β-amylase |
| Example 2 | 87.8 | 247.3 |
| Example 5 | NI[a] | 126.8 |
| Example 6 | 193.7 | 65.0 |
| Example 8 | 268.9 | NI |
| Example 9 | NI | 206.5 |
| Example 10 | 37.3 | 201.4 |
| Example 11 | NI | NI |
| Example 12 | 16.8 | 24.8 | wherein [a]NI denotes the cases where the inhibitory rates were below 20% measured when the concentration of the chalcone derivatives was 200 μM or means that there were no inhibitory activities for α-, or β-amylases.

As shown in Table 3, it can be understood that the chalcone derivatives of Examples 2, 6, 8, 10 and 12 in accordance with the present invention have α-amylase inhibitory activities as the $IC_{50}$ values measured are shown as 87.8, 193.7, 37.3 and 16.8, respectively, and particularly, the chalcone derivatives of Examples 10 and 12 have very excellent α-amylase inhibitory activities.

Experimental Example 3

Measurement of β-Amylase Inhibitory Activities of the Chalcone Derivatives of the Invention Via Analysis of Reducing Sugars β-amylase inhibitory activities were measured in the same manner as Experimental example 2 except for using β-amylases as glycosidase and the $IC_{50}$ values were depicted in Table 3 above.

From the results of table 3, it can be confirmed that the chalcone derivatives of Examples 2, 5, 6, 9, 10 and 12 in accordance with the present invention have β-amylase inhibitory activities as the $IC_{50}$ values measured are shown as 247.3, 126.8, 65.0, 206.5, 201.4 and 24.8, respectively, and particularly, the chalcone derivatives of Example 6 and 12 have very excellent β-amylase inhibitory activities.

From the results of Experimental examples 1 to 3, it can be learned that the chalcone derivatives of the present invention show excellent glycosidase inhibitory activities. Accordingly, the compounds of the present invention can be effectively used in preventing and treating diabetes, obesity, viral diseases, inflammatory diseases, cancers, etc., which may be induced by glycosidases.

Next, the following experiments were carried out in order to measure tyrosinase inhibitory activities and melanin synthesis inhibitory activities of the chalcone derivatives of formula 1 in accordance with the present invention.

Experimental Example 4

Measurement of Tyrosinase Inhibitory Activities

Mushroom tyrosinase was used to identify tyrosinase inhibitory activities of the chalcone derivatives of the present invention. As substrate, tyrosines, a precursor of melanin synthesis, were used to measure tyrosinase activities from the absorbance of DOPA and dopaquinone produced in the process of oxidizing substrate via tyrosinases (Y. Ishihara, J. Antibiotics, 1991, 44, 25).

The mushroom tyrosinases of 250 unit/ml were dissolved in potassium phosphate buffer (0.075 M, pH 6.5) on a 97 well plate and quantified as 100 μl. Subsequently, tyrosines as substrate were dissolved in the potassium phosphate buffer in a concentration of 1.5 mM and quantified as 100 μl. Next, the chalcone derivatives prepared in Examples 2 to 6, 8, 13, 14, 17 and 18 and kojic acid were dissolved in 50% DMSO solvent and quantified as 50 μl, respectively. The samples quantified were reacted at 37° C. for twenty minutes to measure absorbance at 490 nm, thus obtaining tyrosinase inhibitory rates via equation 1 above. Measured $IC_{50}$ values of the chalcone derivatives prepared in Examples 2 to 6, 8, 13, 14, 17 and 18 for tyrosinases were depicted in table 4.

TABLE 4

| Chalcone Derivatives | $IC_{50}$ (μM) |
| --- | --- |
| Example 2 | 4.5 |
| Example 3 | 14.1 |
| Example 4 | 18.9 |
| Example 5 | 16.3 |
| Example 6 | 18.4 |
| Example 8 | 11.8 |
| Example 13 | 15.5 |
| Example 14 | 10.4 |
| Example 17 | 14.6 |

TABLE 4-continued

| Chalcone Derivatives | $IC_{50}$ (μM) |
| --- | --- |
| Example 18 | 18.5 |
| Comparative Example (Kojic Acid) | 21.3 |

As shown in Table 4, it can be understood that the chalcone derivatives of Examples 2 to 6, 8, 13, 14, 17 and 18 in accordance with the present invention have excellent tyrosinase inhibitory activities as the chalcone derivatives show more excellent $IC_{50}$ values than kojic acid.

Experimental Example 5

Measurement of Melanin Synthesis Inhibitory Activities

To identify the melanin synthesis inhibitory activities of the chalcone derivatives of the present invention, whitening effects were measured using B-16 melanoma. 2 ml of B-16 melanoma, derived from black mice, was added to the respective wells in concentration of $2\times10^4$ cells/well on a 6 well plate using DMEM with 10% FBS and cultivated under the conditions of 5% $CO_2$ and 37° C. for twenty four hours. Media were removed after the cultivation and the DMEM used was replaced with DMEM having 10% FBS, 0.2 mM a-MSH and 2 mM theophylline. Subsequently, appropriate amounts of the chalcone compounds of Examples 2 to 6, 8, 13, 14, 17 and 18 were diluted with the same media and added thereto, respectively, to be cultivated under the conditions of 5% CO2 and 37° C. until the cells grew above 80%. The media were removed after the cultivation and the resultant compounds were washed with PBS and processed with tricine to collect cell pellets. Collected pellets were moved to 1.5 ml of Eppendorf tubes to be centrifuged at 5,000 ppm for ten minutes. Then, the pellets in which supernatants were removed were dried in an incubator of 60° C. for twenty four hours. Subsequently, 1N NaOH was added thereto to dissolve melanins in the cells. Dissolved melanins are diluted with appropriate amounts of PBS to measure absorbance at 490 nm, thus obtaining melanin inhibitory rates via Equation 1 above (T. Mosmann, J. Immunol. Methods, 1983, 65, 55; P. R. Gorden, J. Invest. Dermatol., 1989, 92, 565). As a comparative example, the same experiment was carried out using albutin. The $IC_{50}$ values whose melanin synthesis inhibitory rates reached 50% were depicted in Table 5.

TABLE 5

| Chalcone Derivatives | $IC_{50}$ (μM) |
| --- | --- |
| Example 2 | 14.8 |
| Example 3 | 20.6 |
| Example 4 | ND[a] |
| Example 5 | 23.7 |
| Example 6 | 20.3 |
| Example 8 | 12.5 |
| Example 13 | ND |
| Example 14 | 25.6 |
| Example 17 | ND |
| Example 18 | ND |
| Comparative Example (Albutin) | 92.0 | wherein [a]ND denotes the cases where the experiments on the melanin synthesis inhibitory activities in B-16 melanoma were not performed since the cytotoxicity of the compounds was shown as more than 50%.

As shown in Table 5, it can be learned that the chalcone derivatives of Examples 2, 3, 5, 6, 8 and 14 in accordance with the present invention can be effectively used as a skin-whitening composition for inhibiting melanin synthesis as the chalcone derivatives show more excellent $IC_{50}$ values than albutin.

Preparation examples for the compositions of the present invention will now be described hereinafter.

1. Preparation of Powders

| | |
|---|---|
| Chalcone derivative of formula 1 | 2 g |
| Lactose | 1 g |

The above ingredients were mixed and put into an airtight bag, thus preparing a powder medicine.

2. Preparation of Tablet

| | |
|---|---|
| Chalcone derivative of formula 1 | 100 mg |
| Corn starch | 100 mg |
| Lactose | 100 mg |
| Magnesium stearate | 2 mg |

The above ingredients were mixed to prepare a tablet according to an ordinary method for preparing tablets.

3. Preparation of Capsule

| | |
|---|---|
| Chalcone derivative of formula 1 | 100 mg |
| Corn starch | 100 mg |
| Lactose | 100 mg |
| Magnesium stearate | 2 mg |

The above ingredients were mixed and put into a gelatin capsule according to an ordinary method for preparing capsules, thus preparing a capsule.

4. Preparation of Injection

| | |
|---|---|
| Chalcone derivative of formula 1 | 10 μg/ml |
| Weak hydrochloric acid BP | Added until pH became 3.5 |
| Sodium chloride BP for injection | Maximum 1 ml |

The chalcone derivative of formula 1 was dissolved in sodium chloride BP for injection of appropriate capacity, pH of resultant solution was regulated to 3.5 using weak hydrochloric acid BP, the capacity was regulated using sodium chloride BP for injection and stirred sufficiently. The resultant solution was filled in a 5 ml type I ample made of transparent glass and the glass of upper contact portion was melted to be sealed. Then the filled ample was autoclaved at 120° C. for more than fifteen minutes to be sterilized, thus preparing an injection.

5. Preparation of Ointment

| | |
|---|---|
| Chalcone derivative of formula 1 | 5 g |
| Cetylpalmitate | 20 g |
| Cethanol | 40 g |
| Stearylalcohol | 40 g |
| Isopropyl myristate | 80 g |
| Sorbitan monostearate | 20 g |
| Polysorbate | 60 g |
| Propyl parahydroxybenzoate | 1 g |
| Methyl parahydroxybenzoate | 1 g |
| Phosphoric acid and purified water | Quantum satis |

6. Preparation of Cosmetic Compound

| | |
|---|---|
| Chalcone derivative of formula 1 | 10.0 mg |
| Glycerine | 3.0 mg |
| EDTA | 0.05 mg |
| Carboxyvinyl polymer | 0.2 mg |
| Triethanol amine | 0.18 mg |
| Octyldodeces-25 | 0.6 mg |
| Glycerylmonostearate | 1.0 mg |
| Preservative | 0.01 mg |
| Aromatic | 0.01 mg |
| Purified water | Rest |

Although the present invention has been described with reference to certain exemplary embodiments thereof, it will be understood by those skilled in the art that a variety of modifications may be made therein without departing from the spirit or scope of the present invention defined by the appended claims and their equivalents.

INDUSTRIAL APPLICABILITY

Chalcone derivative of formula 1 and pharmaceutically acceptable salts thereof in accordance with the present invention having glycosidase inhibitory activities can be effectively used in preventing and treating diabetes, obesity, viral diseases, inflammatory diseases, cancers, etc., which may be induced by glycosidases. Moreover, the chalcone derivative of formula 1 and pharmaceutically acceptable salts thereof of the invention having excellent tyrosinase and melanin synthesis inhibitory activities can be effectively applied to skin-whitening medicines and cosmetics.

The invention claimed is:

1. A novel chalcone derivative represented by formula 1 below or pharmaceutically acceptable salt thereof:

[Formula 1]

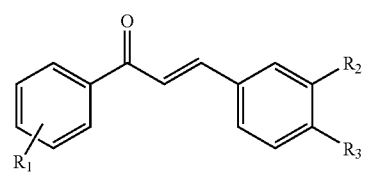

wherein $R_1$ is $R_4NH-$, wherein the substituent $R_1$ is substituted on para-position from $C(=O)$;
$R_2$ is hydrogen or hydroxy group;
$R_3$ is hydroxy group;
$R_4$ is $R_5SO_2-$; and
$R_5$ is $C_1\sim C_5$ alkyl or $C_6\sim C_{10}$ aryl having at least one substituent selected from the group consisting of halogen, nitro and $C_1\sim C_6$ alkyl.

2. The novel chalcone derivative or pharmaceutically acceptable salt thereof as recited in claim 1,
wherein the $R_5$ is selected from the group consisting of methyl, p toluoyl, p-nitrophenyl or p-fluorophenyl.

3. The novel chalcone derivative or pharmaceutically acceptable salt thereof as recited in claim 1,
wherein the chalcone derivative represented by formula 1 is selected from the group consisting of:
1) 4'-(p-toluenesulfonylamino)-3,4-dihydroxychalcone;
2) 4'-(p-toluenesulfonylamino)-4-hydroxychalcone;
4) 4'-(p-nitrobenzenesulfonylamino)-4-hydroxychalcone;
5) 4'-(p-fluorobenzenesulfonylamino)-4-hydroxychalcone;

6) 4'-methanesulfonylamino-4-hydroxychalcone;
10) 4'-(p-nitrobenzenesulfonylamino)-3,4-dihydroxychalcone;
11) 4'-(p-fluorobenzenesulfonylamino)-3,4-dihydroxychalcone;
12) 4'-methanesulfonylamino-3,4-dihydroxychalcone; and
pharmaceutically acceptable salts thereof.

4. A method for preparing a novel chalcone derivative represented by formula 1 of claim 1 comprising:
(a) reacting a compound of formula 2 with sulfonylchloride ($R_4SO_2Cl$) to prepare a compound of formula 3; and
(b) reacting the compound of formula 3 prepared in step (a) with hydroxybenzaldehyde to prepare a compound of formula 1,

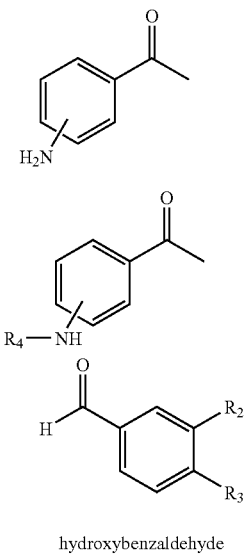

wherein $R_1$, $R_2$, $R_3$, $R_4$ and $R_5$ are as defined in claim 1.

5. A method for inhibiting glycosidase activities in a subject, comprising administering an effective amount of the chalcone derivative represented by formula 1 of claim 1 or pharmaceutically acceptable salt thereof to the subject in need thereof.

6. The method according to claim 5,
wherein the glycosidase is one selected from the group consisting of α-glucosidase, α-amylase and β-amylase.

7. A method for treating diabetes induced by glycosidase in a subject, comprising administering an effective amount of the chalcone derivative represented by formula 1 of claim 1 or pharmaceutically acceptable salt thereof to the subject in need thereof.

8. A method for treating obesity induced by glycosidase in a subject, comprising administering an effective amount of the chalcone derivative represented by formula 1 of claim 1 or pharmaceutically acceptable salt thereof to the subject in need thereof.

9. A method for treating cancers induced by glycosidase in a subject, comprising administering an effective amount of the chalcone derivative represented by formula 1 of claim 1 or pharmaceutically acceptable salt thereof to the subject in need thereof.

10. A method for treating viral diseases induced by glycosidase in a subject, comprising administering an effective amount of the chalcone derivative represented by formula 1 of claim 1 or pharmaceutically acceptable salt thereof to the subject in need thereof.

11. The method according to claim 10,
wherein the viral diseases is caused by human immunodeficiency virus (HIV) or hepatitis B virus (HBV).

12. A method for whitening skin, comprising administering an effective amount of the chalcone derivative represented by formula 1 of claim 1 or pharmaceutically acceptable salt thereof to the skin.

13. The method according to claim 12,
wherein the chalcone derivative is selected from the group consisting of:
1) 4'-(p-toluenesulfonylamino)-3,4-dihydroxychalcone;
2) 4'-(p-toluenesulfonylamino)-4-hydroxychalcone;
4) 4'-(nitrobenzenesulfonylamino)-4-hydroxychalcone;
5) 4'-(p-fluorobenzenesulfonylamino)-4-hydroxychalcone;
6) 4'-methanesulfonylamino-4-hydroxychalcone;
10) 4'-(p-nitrobenzenesulfonylamino)-3,4-dihydroxychalcone;
11) 4'-(p-fluorobenzenesulfonylamino)-3,4-dihydroxychalcone;
12) 4'-methanesulfonylamino-3,4-dihydroxychalcone; and pharmaceutically acceptable salts thereof.

14. A method for inhibiting tyrosinase activities in a subject, comprising administering an effective amount of the chalcone derivative of formula 1 of claim 1 or pharmaceutically acceptable salt thereof to the subject in need thereof.

15. A method for inhibiting melanin synthesis in a subject, comprising administering an effective amount of the chalcone derivative of formula 1 of claim 1 or pharmaceutically acceptable salt thereof to the subject in need thereof.

* * * * *